United States Patent

(12) United States Patent
Elliott et al.

(10) Patent No.: US 8,410,233 B2
(45) Date of Patent: Apr. 2, 2013

(54) METHOD FOR PRODUCING SUPERABSORBERS WITH A LOW RESIDUAL MONOMER CONTENT

(75) Inventors: Mark Elliott, Ludwigshafen (DE); Thomas Daniel, Waldsee (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/058,235

(22) PCT Filed: Aug. 10, 2009

(86) PCT No.: PCT/EP2009/060315
§ 371 (c)(1),
(2), (4) Date: Feb. 9, 2011

(87) PCT Pub. No.: WO2010/018143
PCT Pub. Date: Feb. 18, 2010

(65) Prior Publication Data
US 2011/0136986 A1    Jun. 9, 2011

(30) Foreign Application Priority Data
Aug. 12, 2008 (EP) .................................. 08162218

(51) Int. Cl.
C08F 2/00    (2006.01)
C08F 20/02   (2006.01)
C08F 20/62   (2006.01)

(52) U.S. Cl. ............... 526/220; 526/193; 525/329.8; 525/329.9

(58) Field of Classification Search ............ 525/329.8, 525/329.9; 526/220
See application file for complete search history.

(56) References Cited

U.S. PATENT DOCUMENTS

| 3,936,501 A * | 2/1976 | Greidinger et al. ............. 564/63 |
| RE33,839 E | 3/1992 | Chmelir et al. |
| 6,552,141 B1 | 4/2003 | Chmelir et al. |
| 2004/0132869 A1 * | 7/2004 | Peppmoller et al. ............ 524/13 |
| 2004/0157734 A1 | 8/2004 | Mertens et al. |
| 2007/0293632 A1 * | 12/2007 | Riegel et al. ............ 525/329.9 |
| 2009/0163365 A1 * | 6/2009 | Bentlage et al. ............. 504/360 |
| 2010/0041550 A1 | 2/2010 | Riegel et al. |
| 2011/0042612 A1 | 2/2011 | Riegel et al. |
| 2011/0224361 A1 * | 9/2011 | Daniel et al. ............. 524/556 |

FOREIGN PATENT DOCUMENTS

| DE | 3831261 A1 | 3/1990 |
| JP | 05086251 | 4/1993 |
| SU | 166327 A * | 5/1963 |
| WO | WO-8300289 A1 | 2/1983 |
| WO | WO-95/19191 A1 | 7/1995 |
| WO | WO-9858687 A1 | 12/1998 |
| WO | WO-9926987 A1 | 6/1999 |
| WO | WO-00/55245 A1 | 9/2000 |
| WO | WO-02096953 A1 | 12/2002 |
| WO | WO-2004018005 A1 | 3/2004 |
| WO | WO-2004018006 A1 | 3/2004 |
| WO | WO-2006119828 A1 | 11/2006 |
| WO | WO 2006119828 A1 * | 11/2006 |
| WO | WO-2008055856 A1 | 5/2008 |
| WO | WO-2008/092843 A1 | 8/2008 |
| WO | WO-2008092842 A | 8/2008 |

OTHER PUBLICATIONS

Graham, Andrew T., et al. Modern Superabsorbent Polymer Technology, "Commercial Processes for the Manufacture of Superabsorbent Polymers." New York: John Wiley & Sons, Inc., 1998, pp. 69-117.
International Search Report in International Application No. PCT/EP2009/060315, dated Oct. 27, 2009.

* cited by examiner

Primary Examiner — Karuna P Reddy
(74) Attorney, Agent, or Firm — Marshall, Gerstein & Borun LLP

(57) ABSTRACT

To prepare superabsorbents with a low residual monomer content, a salt of urea with an inorganic acid is added to the monomer mixture before or during the polymerization or to the polymer after the polymerization but before a heat treatment which follows the polymerization.

11 Claims, No Drawings

METHOD FOR PRODUCING SUPERABSORBERS WITH A LOW RESIDUAL MONOMER CONTENT

CROSS-REFERENCE TO RELATED APPLICATIONS

This is the U.S. national phase of International Application No. PCT/EP2009/060315, filed Aug. 10, 2009, which claims the benefit of European patent Application No. 08162218.5, filed Aug. 12, 2008.

The present invention relates to a superabsorbent with low residual monomer content, to a process for production thereof and to the use thereof, and to hygiene articles comprising it.

Superabsorbents are known. For such materials, names such as "high-swellability polymer", "hydrogel" (often also used for the dry form), "hydrogel forming polymer", "water-absorbing polymer", "absorbent gel-forming material", "swellable resin", "water-absorbing resin", "water-absorbing polymer" or the like are also in common use. The substances in question are crosslinked hydrophilic polymers, especially polymers of (co)polymerized hydrophilic monomers, graft (co)polymers of one or more hydrophilic monomers on a suitable graft base, crosslinked cellulose ethers or starch ethers, crosslinked carboxymethylcellulose, partly crosslinked polyalkylene oxide or natural products which are swellable in aqueous liquids, for example guar derivatives, of which superabsorbents based on partly neutralized acrylic acid are the most widespread. The essential properties of superabsorbents are their abilities to absorb several times their own weight of aqueous liquids and not to release the liquid again even under a certain pressure. The superabsorbent, which is used in the form of a dry powder, is converted to a gel when it absorbs liquid, and correspondingly to a hydrogel when it absorbs water as usual. Crosslinking is essential for synthetic superabsorbents and is an important difference from customary pure thickeners, since it leads to the insolubility of the polymers in water. Soluble substances would not be usable as superabsorbents. By far the most important field of use of superabsorbents is the absorption of body fluids. Superabsorbents are used, for example, in diapers for infants, incontinence products for adults or feminine hygiene products. Other fields of use are, for example, as water-retaining agents in market gardening, as water stores for protection from fire, for liquid absorption in food packaging, or quite generally for absorbing moisture.

Superabsorbents can absorb several times their own weight of water and retain it under a certain pressure. In general, such a superabsorbent has a CRC ("centrifuge retention capacity", see below for test method) of at least 5 g/g, preferably at least 10 g/g and more preferably at least 15 g/g. A "superabsorbent" may also be a mixture of different individual superabsorbent substances or a mixture of components which exhibit superabsorbent properties only when they interact; it is not so much the substance composition as the superabsorbent properties that are important here.

What is important for a superabsorbent is not just its absorption capacity but also the ability to retain liquid under pressure (retention) and liquid transport in the swollen state. Swollen gel can hinder or prevent liquid transport to as yet unswollen superabsorbent ("gel blocking"). Good transport properties for liquids are possessed, for example, by hydrogels which have a high gel strength in the swollen state. Gels with only a low gel strength are deformable under an applied pressure (body pressure), block pores in the superabsorbent/cellulose fiber suction body and thus prevent further absorption of liquid. An increased gel strength is generally achieved through a higher degree of crosslinking, which, however, reduces the absorption capacity of the product. An elegant method of increasing the gel strength is that of increasing the degree of crosslinking at the surface of the superabsorbent particles compared to the interior of the particles. To this end, superabsorbent particulars which have usually been dried in a surface postcrosslinking step and have an average crosslinking density are subjected to additional crosslinking in a thin surface layer of the particles thereof. The surface postcrosslinking increases the crosslinking density in the shell of the superabsorbent particles, which raises the absorption under compressive stress to a higher level. While the absorption capacity in the surface layer of the superabsorbent particles falls, their core, as a result of the presence of mobile polymer chains, has an improved absorption capacity compared to the shell, such that the shell structure ensures improved liquid conduction, without occurrence of gel blocking. It is likewise known that superabsorbents which are relatively highly crosslinked overall can be obtained and the degree of crosslinking in the interior of the particles can subsequently be reduced compared to an outer shell of the particles.

Processes for preparing superabsorbents are also known. Superabsorbents based on acrylic acid, which are the most common on the market, are produced by free-radical polymerization of acrylic acid in the presence of a crosslinker (the "interior crosslinker"), the acrylic acid being neutralized to a certain degree before, after or partly before and partly after the polymerization, typically by adding alkali, usually an aqueous sodium hydroxide solution. The polymer gel thus obtained is comminuted (according to the polymerization reactor used, this can be done simultaneously with the polymerization) and dried. The dry powder thus obtained (the "base polymer") is typically postcrosslinked on the surface of the particles, by reacting it with further crosslinkers, for instance organic crosslinkers or polyvalent cations, for example aluminum (usually used in the form of aluminum sulfate) or both, in order to obtain a more highly crosslinked surface layer compared to the particle interior.

A problem which often occurs in the case of superabsorbents is discoloration, which occurs in the course of storage under elevated temperature or elevated air humidity. Such conditions often occur in the case of storage of superabsorbents in tropical or subtropical countries. Superabsorbents tend to yellow under such conditions; they may even assume a brown or even almost black color. This discoloration of the actually colorless superabsorbent powder is unsightly and undesired, since it is visible especially in the desired thin hygiene products, and consumers reject unsightly hygiene products. The cause of the discoloration has not been entirely clarified, but reactive compounds such as residual monomers from the polymerization, impurities in the neutralizing agent or the initiators, the use of some initiators, surface postcrosslinkers or stabilizers, and impurities in the monomers used appear to play a role.

A further problem in the production of superabsorbents is to avoid undesirably high proportions of unconverted monomers, known as residual monomers. In excessively high concentrations, these may quite possibly be of toxicological concern; in addition, they are also reactive and may lead to undesired discoloration.

In addition, an undesirably high content of iron ions in the superabsorbent may lead to problems. Iron impurities may lead to a comparatively high content of residual monomers and a greater yellowing tendency of the superabsorbent. A frequent source of iron in common superabsorbents is sodium hydroxide solution, which is used for partial neutralization of acrylic acid. Sodium hydroxide solution is available in various purities which also differ in the iron content, but the cost also increases with the purity, which makes the superabsorbent less economically viable.

Fredric L. Buchholz and Andrew T. Graham (eds.) give, in: "Modern Superabsorbent Polymer Technology", J. Wiley & Sons, New York, U.S.A./Wiley-VCH, Weinheim, Germany, 1997, ISBN 0-471-19411-5, a comprehensive overview of superabsorbents, properties thereof and processes for producing superabsorbents.

WO 2008/055856 A1 teaches the prevention of discoloration of a superabsorbent which is caused by an excessively high iron content of sodium hydroxide solution which is used for partial neutralization of the acrylic acid in the course of preparation of the superabsorbent, by adding phosphoric acid or phosphate salts, especially alkali metal phosphates. JP 05/086 251 A teaches the use of phosphoric acid derivatives or salts thereof, especially 1-hydroxyethylidene-1,1-diphosphonic acid, ethylenediaminetetra(methylenephosphonic acid), diethylenetriaminepenta(methylenephosphonic acid) or the alkali metal or ammonium salts thereof as stabilizers of superabsorbents against discoloration. WO 00/55245 A1 teaches the stabilization of superabsorbents against discoloration by treatment with an inorganic reducer agent and optionally a metal salt. The inorganic reducing agent is typically a hypophosphite, phosphite, bisulfite or sulfite. The metal salt is typically a colorless (the property of "colorless" is often also referred to simply as "white") phosphate, acetate or lactate, but not a halide.

The prior international patent application PCT/EP2008/051009 teaches the addition of a basic salt of a divalent metal cation to superabsorbents, in order to increase the stability against discoloration among other reasons. The prior international patent application PCT/EP2008/051010 discloses the use of carboxylic salts and/or basic salts of trivalent metal cations for the same purpose.

DE 38 31 261 A1 teaches the addition of nitrogen-containing, thermally decomposable blowing agents during the superabsorbent production before drying in order to obtain a loose and readily grindable resin. Urea is specified as a possible blowing agent. According to the teaching of WO 02/096 953 A1, a blowing agent such as urea can be added to a superabsorbent based on carboxypolysaccharide, in order to generate additional porosity. WO 2006/119 828 A1 teaches a hybrid material composed of polyacrylate superabsorbent and inorganic solid particles, which is suitable as a plant substrate. It is possible in this case to add particular organic additives, including urea, to the hybrid material, more particularly to the superabsorbent, either as a $CO_2$ source during the polymerization, i.e. as a blowing agent, or else as a fertilizing nitrogen source.

WO 98/58 687 A1 teaches the use of urea as a possible internal crosslinker for polycarboxypolysaccharide superabsorbents. WO 2004/018 005 A1 and WO 2004/018 006 A1 specify urea as a possible surface postcrosslinker for polyacrylate superabsorbents.

WO 95/17 417 A1 discloses that the fluid absorption properties of polysaccharides can be improved by a urea coating.

WO 95/19191 A1 mentions urea in a list of nonpolymeric improvers which improve blood absorption by superabsorbents.

WO 83/00 289 A1 discloses mixtures of superabsorbent and an additive, which may also be urea, as an absorbent for blood and serous body fluids.

WO 99/26 987 A1 describes the reduction of the residual monomer level in superabsorbents by adding a salt of a nitrogen compound to the monomer mixture and then heating the polymer at temperatures of from 120 to 240° C. The nitrogen compounds specified are ammonia, hydroxylamine, aliphatic, cycloaliphatic and aromatic mono- and polyamines, heterocyclic amines and alkanolamines. The anion of the salt is an anion of an inorganic or organic acid.

It is an object of the present invention a novel or improved process for producing superabsorbents with low residual monomer content and at most tolerable color, if any. The use properties of the superabsorbent, especially its absorbency for fluid, even under pressure, the free swellability and its ability to conduct liquid, but also its free flow, should at least not be impaired significantly, if at all.

The object is achieved by a polymerization process for preparing superabsorbents, by adding a salt of urea with an inorganic acid to the monomer mixture before or during the polymerization, or to the polymer after the polymerization but before a heat treatment which follows the polymerization. Additionally found have been the superabsorbents obtainable by this process, uses of this superabsorbent, and hygiene articles which comprise this superabsorbent.

The process according to the invention leads to superabsorbents with low residual monomer content and low discoloration tendency, without their use properties being impaired.

The polymerization process according to the invention differs from known polymerization processes for preparing superabsorbents only in that a salt of urea with an inorganic acid is added to the monomer mixture before, during or after the polymerization, but before a heat treatment which follows the polymerization. In other words, any known polymerization process for producing superabsorbents can be executed by adding a salt of urea with an inorganic acid in an inventive manner.

It is possible to use any salt of urea with an inorganic acid, including mixtures of such salts. In other words, "a salt of urea with an inorganic acid" is also understood to mean a mixture of such salts. Preference is given to using an inorganic acid which does not have reducing properties, i.e. does not reduce any other substances under customary conditions. Preference is also given to using a nonoxidizing acid, i.e. an acid which does not oxidize any other substances under customary conditions. Particularly preferred inorganic acids are especially sulfuric acid, phosphoric acid, polyphosphoric acids, the hydrohalic acids, including especially hydrofluoric acid and hydrochloric acid, the latter being preferred among the hydrohalic acids. A very particularly preferred acid is phosphoric acid. In other words: in a very particularly preferred embodiment of the process according to the invention, urea phosphate is added before, during or after the polymerization, but before a heat treatment step which follows the polymerization.

Preference is given to adding the urea salt (including mixtures of urea salts) with an inorganic acid before or during the polymerization, more preferably before the polymerization. In other words, the salt of urea with an inorganic acid is more preferably added to the monomer mixture to be polymerized. However, it is also possible to add the salt only after the start of the polymerization or to add it to the finished polymer. However, this increases the technical complexity of distributing the salt homogeneously in the polymer, which impairs the economic viability.

In the customary processes for producing superabsorbents, the polymerization is effected as a solution polymerization in water or in a suspension of aqueous monomer mixture in an organic suspension medium. After the polymerization, a heat treatment step—usually known simply as "drying"—is therefore generally required in order to remove the water present and to produce dry superabsorbent capable of absorbing fluid.

Even though heat is released in the course of polymerization, the polymerization itself is not understood to be a heat treatment step. Even in cases in which there should be no water to remove, the superabsorbent would typically pass through a heat treatment step for surface postcrosslinking. In all cases, in the process according to the invention, the salt of urea with an inorganic acid is added before a heat treatment step, preferably before the drying. Should, in a special case in the process to be employed, no heat treatment step whatever be provided, the salt of urea with an inorganic acid is nevertheless added before, during or after the polymerization, preferably before or during the polymerization and more preferably before the polymerization.

In general, the salt of urea with an inorganic acid is added in an amount of at least 0.01% by weight, preferably of at least 0.1% by weight, more preferably of at least 0.2% by weight and most preferably of at least 0.3% by weight, and generally of at most 5% by weight, preferably at most 2.5% by weight, more preferably at most 1.5% by weight and most preferably at most 1.0% by weight, based in each case on the finished superabsorbent.

A preferred polymerization process according to the invention for preparing acrylate superabsorbents is the aqueous solution polymerization of a monomer mixture comprising a) at least one ethylenically unsaturated monomer which bears acid groups and is optionally present at least partly in salt form,
b) at least one crosslinker,
c) at least one initiator,
d) optionally one or more ethylenically unsaturated monomers copolymerizable with the monomers specified under a),
e) optionally one or more water-soluble polymers and
f) a salt of urea with an inorganic acid.

The monomers a) are preferably water-soluble, i.e. the solubility in water at 23° C. is typically at least 1 g/100 g of water, preferably at least 5 g/100 g of water, more preferably at least 25 g/100 g of water, most preferably at least 35 g/100 g of water.

Suitable monomers a) are, for example, ethylenically unsaturated carboxylic acids or salts thereof, such as acrylic acid, methacrylic acid, maleic acid, maleic anhydride and itaconic acid or salts thereof. Particularly preferred monomers are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 2002/055469 A1, WO 2003/078378 A1 and WO 2004/035514 A1. A suitable monomer a) is, for example, acrylic acid purified according to WO 2004/035514 A1 comprising 99.8460% by weight of acrylic acid, 0.0950% by weight of acetic acid, 0.0332% by weight of water, 0.0203% by weight of propionic acid, 0.0001% by weight of furfurals, 0.0001% A by weight of maleic anhydride, 0.0003% by weight of diacrylic acid and 0.0050% by weight of hydroquinone monomethyl ether.

The proportion of acrylic acid and/or salts thereof in the total amount of monomers a) is preferably at least 50 mol %, more preferably at least 90 mol %, most preferably at least 95 mol %.

The monomer solution comprises preferably at most 250 ppm by weight, preferably at most 130 ppm by weight, more preferably at most 70 ppm by weight and preferably at least 10 ppm by weight, more preferably at least 30 ppm by weight, especially around 50 ppm by weight, of hydroquinone monoether, based in each case on the unneutralized monomer a); neutralized monomer a), i.e. a salt of the monomer a), is considered for arithmetic purposes as unneutralized monomer. For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 530 438 A1, di- and triacrylates, as described in EP 547 847 A1, EP 559 476 A1, EP 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/5830 A1 and WO 2002/32962 A2.

Preferred crosslinkers b) are pentaerythrityl triallyl ether, tetraallyloxyethane, methylenebismethacrylamide, 10 to 20-tuply ethoxylated trimethylolpropane nacrylate, 10 to 20-tuply ethoxylated trimethylolethane triacrylate, more preferably 15-tuply ethoxylated trimethylolpropane triacrylate, polyethylene glycol diacrylates with from 4 to 30 ethylene oxide units in the polyethylene glycol chain, trimethylolpropane triacrylate, di- and triacrylates of 3 to 30-tuply ethoxylated glycerol, more preferably di- and triacrylates of 10-20-tuply ethoxylated glycerol, and triallylamine. The polyols incompletely esterified with acrylic acid may also be present here in the form of Michael adducts with themselves, as a result of which tetraacrylates, pentaacrylates or even higher acrylates may also be present.

Very particularly preferred crosslinkers b) are the polyethoxylated and/or -propoxylated glycerols which have been esterified with acrylic acid or methacrylic acid to give di- or triacrylates, as described, for example, in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably from 0.05 to 1.5% by weight, more preferably from 0.1 to 1% by weight, most preferably from 0.3 to 0.6% by weight, based in each case on monomer a). With rising crosslinker content, the centrifuge retention capacity (CRC) falls and the absorption under a pressure of 0.3 psi (AUL0.3 psi) rises.

The initiators c) may be all compounds which generate free radicals under the polymerization conditions, for example thermal initiators, redox initiators, photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. The reducing component used is, however, preferably a mixture of the sodium salt of 2-hydroxy-2-sulfinatoacetic acid, the disodium salt of 2-hydroxy-2-sulfonatoacetic acid and sodium bisulfite (as Brüggolit® FF6M or Brüggolit® FF7, alternatively BRUGGOLITE® FF6M or BRUGGOLITE® FF7 obtainable from L. Brüggemann KG, Salzstrasse 131, 74076 Heilbronn, Germany, wvvw.brueggemann.com).

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate, maleic acid and maleic anhydride.

The water-soluble polymers e) used may be polyvinyl alcohol, polyvinylpyrrolidone, starch, starch derivatives, modified cellulose, such as methylcellulose or hydroxyethylcellulose, gelatin, polyglycols or polyacrylic acids, preferably starch, starch derivatives and modified cellulose.

Salts of urea with an inorganic acid f) are described above. In particular, salts of urea with sulfuric acid, phosphoric acid, hydrohalic acids, including especially hydrofluoric acid and hydrochloric acid, the latter being preferred among the hydrohalic acids. Very particular preference is given to adding urea phosphate.

Typically, an aqueous monomer solution is used. The water content of the monomer solution is preferably from 40 to 75% by weight, more preferably from 45 to 70% by weight, most preferably from 50 to 65% by weight. It is also possible to use monomer suspensions, i.e. oversaturated monomer solutions. With rising water content, the energy requirement in the subsequent drying rises, and, with falling water content, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

The monomer mixture may comprise further components. Examples of further components used in monomer mixtures of this kind are, for instance, chelating agents, in order to keep metal ions in solution.

Suitable polymerization reactors are, for example, kneading reactors or belt reactors. In the kneader, the polymer gel formed in the polymerization of an aqueous monomer solution or suspension is comminuted continuously by, for example, contrarotatory stirrer shafts, as described in WO 2001/38402 A1. Polymerization on a belt is described, for example, in DE 38 25 366 A1 and U.S. Pat. No. 6,241,928. Polymerization in a belt reactor forms a polymer gel, which has to be comminuted in a further process step, for example in a meat grinder, extruder or kneader. However, it is also possible to produce spherical superabsorbent particles by suspension, spray or droplet polymerization processes. The use of urea phosphate, which is particularly preferred in accordance with the invention, is particularly advantageous in polymerization processes, for example a kneading reactor or a droplet polymerization, with relatively short polymerization time.

The acid groups of the resulting polymer gels have typically been partially neutralized. Neutralization is preferably carried out at the monomer stage; in other words, salts of the monomers bearing acid groups or, to be precise, a mixture of monomers bearing acid groups and salts of the monomers bearing acid groups ("partly neutralized acid") are used as component a) in the polymerization. This is typically done by mixing the neutralizing agent as an aqueous solution or preferably also as a solid into the monomer mixture intended for polymerization or preferably into the monomer bearing acid groups or a solution thereof. The degree of neutralization is preferably from 25 to 95 mol %, more preferably from 50 to 80 mol %, most preferably from 65 to 72 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metal cations are sodium and potassium, but very particular preference is given to sodium hydroxide, sodium carbonate or sodium hydrogencarbonate and also mixtures thereof.

However, it is also possible to carry out neutralization after the polymerization, at the stage of the polymer gel formed in the polymerization. It is also possible to neutralize up to 40 mol %, preferably from 10 to 30 mol % and more preferably from 15 to 25 mol % of the acid groups before the polymerization by adding a portion of the neutralizing agent actually to the monomer solution and setting the desired final degree of neutralization only after the polymerization, at the polymer gel stage. When the polymer gel is neutralized at least partly after the polymerization, the polymer gel is preferably comminuted mechanically, for example by means of an extruder, in which case the neutralizing agent can be sprayed, sprinkled or poured on and then carefully mixed in. To this end, the gel mass obtained can be repeatedly extruded for homogenization.

However, preference is given to performing the neutralization at the monomer stage. In other words: in a very particularly preferred embodiment, the monomer a) used is a mixture of from 25 to 95 mol %, more preferably from 50 to 80 mol %, more preferably from 65 to 72 mol %, of salt of the monomer bearing acid groups, and the remainder to 100 mol % of monomer bearing acid groups. This mixture is, for example, a mixture of sodium acrylate and acrylic acid or a mixture of potassium acrylate and acrylic acid.

In a preferred embodiment, the neutralizing agent used for the neutralization is one whose iron content is generally below 10 ppm by weight, preferably below 2 ppm by weight and more preferably below 1 ppm by weight. Likewise desired is a low content of chloride and anions of oxygen acids of chlorine. A suitable neutralizing agent is, for example, the 50% by weight sodium hydroxide solution or potassium hydroxide solution which is typically traded as "membrane grade"; even more pure and preferred, but also more expensive, is the 50% by weight sodium hydroxide solution or potassium hydroxide solution typically traded as "amalgam grade" or "mercury process". The polymer gel obtained from the aqueous solution polymerization and, if appropriate, subsequent neutralization is then preferably dried with a belt drier until the residual moisture content is preferably from 0.5 to 15% by weight, more preferably from 1 to 10% by weight, most preferably from 2 to 8% by weight (see below for test method for the residual moisture or water content). In the case of too high a residual moisture content, the dried polymer gel has too low a glass transition temperature Tg and can be processed further only with difficulty. In the case of too low a residual moisture content, the dried polymer gel is too brittle and, in the subsequent comminution steps, undesirably large amounts of polymer particles with too low a particle size ("fines") are obtained. The solids content of the gel before drying is generally from 25 to 90% by weight, preferably from 30 to 80% by weight, more preferably from 35 to 70% by weight, most preferably from 40 to 60% by weight. Optionally, however, it is also possible to dry using a fluidized bed drier or a heatable mixer with a mechanical mixing unit, for example a paddle drier or a similar drier with mixing tools of different design. Optionally, the drier can be operated under nitrogen or another nonoxidizing inert gas or at least under reduced partial oxygen pressure in order to prevent oxidative yellowing processes. In general, however, even sufficient venting and removal of water vapor leads to an acceptable product. A very short drying time is generally advantageous with regard to color and product quality. In the case of the common belt driers, in a customary operating mode, a temperature of the gas used for drying of at least 50° C., preferably at least 80° C. and more preferably of at least 100° C., and generally of at most 250° C., preferably at most 200° C. and more preferably of at most 180° C., is established for this purpose. Suitable belt driers often have several chambers; the temperature in these chambers may be different. In each drier type, the operating conditions should be selected overall in a known manner such that the drying outcome desired is achieved.

During the drying, the residual monomer content in the polymer particles is also reduced, and last residues of the initiator are destroyed.

Thereafter, the dried polymer gel is ground and classified, apparatus usable for the grinding typically including single- or multistage roll mills, preferably two- or three-stage roll mills, pin mills, hammer mills or vibratory mills. Oversize gel lumps which often still have not dried on the inside are elastomeric, lead to problems in the grinding and are preferably removed before the grinding, which can be done in a simple manner by wind sifting or by means of a screen ("protective screen" for the mill). In view of the mill used, the mesh size of the screen should be selected such that a minimum level of disruption resulting from oversize, elastomeric particles occurs.

Excessively large, insufficiently finely ground superabsorbent particles are perceptible as coarse particles in their predominant use, in hygiene products such as diapers; they also lower the mean initial swell rate of the superabsorbent. Both are undesired. Advantageously, coarse-grain polymer particles are therefore removed from the product. This is typically done by classification processes, for example wind sifting, or by screening through a screen with a mesh size of at most 1000 µm, preferably at most 900 µm, more preferably at most 850 µm and most preferably at most 800 µm. For example, screens of mesh size 700 µm, 650 µm or 600 µm are used. The coarse polymer particles ("oversize") removed may, for cost optimization, be sent back to the grinding and screening cycle or be processed further separately.

Polymer particles with too low a particle size lower the permeability (SFC). Advantageously, fine polymer particles are therefore also removed in this classification. This can, if screening is effected, conveniently be used through a screen of mesh size at most 300 µm, preferably at most 200 µm, more preferably at most 150 µm and most preferably at most 100 µm. The fine polymer particles ("undersize" or "fines") removed can, for cost optimization, be sent back as desired to the monomer stream, to the polymerizing gel or to the fully polymerized gel before the drying of the gel.

The mean particle size of the polymer particles removed as the product fraction is generally at least 200 µm, preferably at least 250 µm and more preferably at least 300 µm, and generally at most 600 µm and more preferably at most 500 µm. The proportion of particles with a particle size of at least 150 µm is generally at least 90% by weight, more preferably at least 95% by weight and most preferably at least 98% by weight. The proportion of particles with a particle size of at most 850 µm is generally at least 90% by weight, more preferably at least 95% by weight and most preferably at least 98% by weight.

The polymer thus prepared has superabsorbent properties and is covered by the term "superabsorbent". Its CRC is typically comparatively high, but its AUL or SFC comparatively low. A surface nonpostcrosslinked superabsorbent of this type is often referred to as "base polymer" to distinguish it from a surface postcrosslinked superabsorbent produced therefrom.

To further improve the properties, especially increase the AUL and SFC values (which lowers the CRC value), the superabsorbent particles can be surface postcrosslinked. Suitable postcrosslinkers are compounds which comprise groups which can form bonds with at least two functional groups of the superabsorbent particles. In the case of the acrylic acid/sodium acrylate-based superabsorbents prevalent on the market, suitable surface postcrosslinkers are compounds which comprise groups which can form bonds with at least two carboxylate groups. Preferred postcrosslinkers are amide/acetals or carbamates of the general formula (I)

in which
$R^1$ is $C_1$-$C_{12}$-alkyl $C_2$-$C_{12}$-hydroxyalkyl, $C_2$-$C_{12}$-alkenyl or $C_6$-$C_{12}$-aryl,
$R^2$ is X or $OR^6$,
$R^6$ is hydrogen, $C_1$-$C_{12}$-alkyl, $C_2$-$C_{12}$-hydroxyalkyl, $C_2$-$C_{12}$-alkenyl or $C_6$-$C_{12}$-aryl, or X,
$R^4$ is $C_1$-$C_{12}$-alkyl, $C_2$-$C_{12}$-hydroxyalkyl, $C_2$-$C_{12}$-alkenyl or $C_6$-$C_{12}$-aryl,
$R^5$ is hydrogen, $C_1$-$C_{12}$-alkyl, $C_2$-$C_{12}$-hydroxyalkyl, $C_2$-$C_{12}$-alkenyl, $C_1$-$C_{12}$-acyl or $C_6$-$C_{12}$-aryl,
$R^6$ is $C_1$-$C_{12}$-alkyl, $C_2$-$C_{12}$-hydroxyalkyl, $C_2$-$C_{12}$-alkenyl or $C_6$-$C_{12}$-aryl and
X is a carbonyl oxygen for the $R^2$ and $R^3$ radicals together, where $R^1$ and $R^4$ and/or $R^5$ and $R^6$ may be a bridged $C_2$-$C_6$-alkanediyl and where the abovementioned $R^1$ to $R^6$ radicals may also have a total of from one to two free valences and may be joined to at least one suitable base structure by these free valances,
or polyhydric alcohols, the polyhydric alcohol preferably having a molecular weight of less than 100 g/mol, preferably of less than 90 g/mol, more preferably of less than 80 g/mol, most preferably of less than 70 g/mol, per hydroxyl group, and no vicinal, geminal, secondary or tertiary hydroxyl groups, and polyhydric alcohols are either diols of the general formula (IIa)

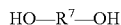 (IIa)

in which $R^7$ is either an unbranched dialkyl radical of the formula $—(CH_2)_n—$ where n is an integer from 3 to 20, preferably from 3 to 12, and both hydroxyl groups are terminal, or $R^7$ is an unbranched, branched or cyclic dialkyl radical, or polyols of the general formula (IIb)

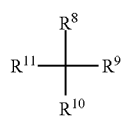 (IIb)

in which the $R^8$, $R^9$, $R^{10}$, $R^{11}$ radicals are each independently hydrogen, hydroxyl, hydroxymethyl, hydroxyethyloxymethyl, 1-hydroxyprop-2-yloxymethyl, 2-hydroxypropyloxymethyl, methyl, ethyl, n-propyl, isopropyl, n-butyl, n-pentyl, n-hexyl, 1,2-dihydroxyethyl, 2-hydroxyethyl, 3-hydroxypropyl or 4-hydroxybutyl, and the total of 2, 3 or 4, preferably 2 or 3, hydroxyl groups are present, and not more than one of the $R^8$, $R^9$, $R^{10}$, and $R^{11}$ radicals is hydroxyl, or cyclic carbonates of the general formula (III)

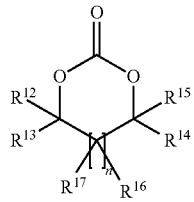 (III)

in which $R^{12}$, $R^{13}$, $R^{14}$, $R^{15}$, $R^{16}$ and $R^{17}$ are each independently hydrogen, methyl, ethyl, n-propyl, isopropyl, n-butyl, sec-butyl or isobutyl, and n is either 0 or 1, or bisoxazolines of the general formula (IV)

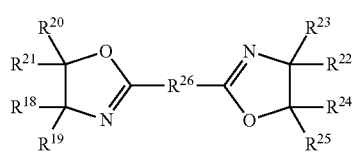 (IV)

in which $R^{18}$, $R^{19}$, $R^{20}$, $R^{21}$, $R^{22}$, $R^{23}$, $R^{24}$ and $R^{25}$ are each independently hydrogen, methyl, ethyl, n-propyl, isopropyl, n-butyl, sec-butyl or isobutyl, and $R^{26}$ is a single bond, a linear, branched or cyclic $C_2$-$C_{12}$-dialkyl radical, or a polyalkoxydiyl radical which is formed from one to ten ethylene oxide and/or propylene oxide units, as possessed, for example, by polyglycoldicarboxylic acids.

Preferred crosslinkers of the general formula (II) are 2-oxazolidones such as 2-oxazolidone and N-(2-hydroxyethyl)-2-oxazolidone, N-methyl-2-oxazolidone, N-acyl-2-oxazolidones such as N-acetyl-2-oxazolidone, 2-oxotetrahydro-1,3-oxazine, bicyclic amide acetals such as 5-methyl-1-aza-4,6-dioxabicyclo[3.3.0]octane, 1-aza-4,6-dioxa-bicyclo[3.3.0]octane and 5-isopropyl-1-aza-4,6-dioxabicyclo[3.3.0]octane, bis-2-oxazolidones and poly-2-oxazolidones.

Particularly preferred postcrosslinkers of the general formula (I) are 2-oxazolidone, N-methyl-2-oxazolidone, N-(2-hydroxyethyl)-2-oxazolidone and N-hydroxypropyl-2-oxazolidone.

Preferred postcrosslinkers of the general formula (IIa) are 1,3-propanediol, 1,5-pentanediol, 1,6-hexanediol and 1,7-heptanediol. Further examples of postcrosslinkers of the formula (IIa) are 1,3-butanediol, 1,8-octanediol, 1,9-nonanediol and 1,10-decanediol.

The diols are preferably water-soluble, the diols of the general formula (IIa) being water-soluble at 23° C. to an extent of at least 30% by weight, preferably to an extent of at least 40% by weight, more preferably to an extent of at least 50% by weight, most preferably at least to an extent of 60% by weight, for example 1,3-propanediol and 1,7-heptanediol. Even more preferred are those postcrosslinkers which are liquid at 25° C.

Preferred postcrosslinkers of the general formula (IIb) are butane-1,2,3-triol, butane-1,2,4-triol, glycerol, trimethylolpropane, trimethylolethane, pentaerythritol, 1- to 3-tuply (per molecule) ethoxylated glycerol, trimethylolethane or trimethylolpropane and 1- to 3-tuply (per molecule) propoxylated glycerol, trimethylolethane or trimethylolpropane. Additionally preferred are 2-tuply ethoxylated or propoxylated neopentyl glycol.

Particular preference is given to 2-tuply and 3-tuply ethoxylated glycerol, neopentyl glycol, 2-methyl-1,3-propanediol and trimethylolpropane.

Preferred polyhydric alcohols (IIa) and (IIb) have, at 23° C., a viscosity of less than 3000 mPas, preferably less than 1500 mPas, preferentially less than 1000 mPas, more preferably less than 500 mPas, most preferably less than 300 mPas.

Particularly preferred postcrosslinkers of the general formula (III) are ethylene carbonate and propylene carbonate.

A particularly preferred postcrosslinker of the general formula (IV) is 2,2'-bis(2-oxazoline).

The preferred postcrosslinkers minimize side reactions and subsequent reactions which lead to volatile and hence malodorous compounds. The superabsorbents produced with the preferred postcrosslinkers are therefore odor-neutral even in the moistened state.

It is possible to use an individual postcrosslinker from the above selection or any mixtures of different postcrosslinkers.

The postcrosslinker is generally used in an amount of at least 0.001% by weight, preferably of at least 0.02% by weight, more preferably of at least 0.05% by weight, and generally at most 2% by weight, preferably at most 1% by weight, more preferably at most 0.3% by weight, for example at most 0.15% by weight or at most 0.095% by weight, based in each case on the mass of the base polymer.

The postcrosslinking is typically carried out in such a way that a solution of the postcrosslinker is sprayed onto the dried base polymer particles. After the spray application, the polymer particles coated with postcrosslinker are dried thermally, and the postcrosslinking reaction may take place either before or during the drying. If surface postcrosslinkers with polymerizable groups are used, the surface postcrosslinking can also be effected by means of free-radically induced polymerization of such groups by means of common free-radical formers or else by means of high-energy radiation, for example UV light. This can be done in parallel or instead of the use of postcrosslinkers which form covalent or ionic bonds to functional groups at the surface of the base polymer particles.

The spray application of the postcrosslinker solution is preferably carried out in mixers with moving mixing tools, such as screw mixers, disk mixers or paddle mixers, or mixers with other mixing tools. Particular preference is given, however, to vertical mixers. However, it is also possible to spray on the postcrosslinker solution in a fluidized bed. Suitable mixers are, for example, obtainable as Pflugschar® plowshare mixers from Gebr. Lödige Maschinenbau GmbH, Elsener-Strasse 7-9, 33102 Paderborn, Germany, or as Schugi® Flexomix® mixers, Vrieco-Nauta® mixers or Turbulizer® mixers from Hosokawa Micron BV, Gildenstraat 26, 7000 AB Doetinchem, the Netherlands.

The spray nozzles usable are not subject to any restriction. Suitable nozzles and atomization systems are described, for example, in the following references: Zerstäuben von Flüssigkeiten [Atomization of Liquids], Expert-Verlag, vol. 660, Reihe Kontakt & Studium, Thomas Richter (2004), and in Zerstäubungstechnik [Atomization Technology], Springer-Verlag, VDI-Reihe, Günter Wozniak (2002). It is possible to use mono- and polydisperse spray systems. Among the polydisperse systems, one-substance pressurized nozzles (jet- or lamellar-forming), rotational atomizers, two-substance atomizers, ultrasound atomizers and impingement nozzles. In the case of the two-substance atomizers, the liquid phase can be mixed with the gas phase either internally or externally. The spray profile of the nozzles is uncritical and may assume any desired form, for example a round jet, flat jet, wide angle round beam or circular ring spray profile. It is advantageous to use a nonoxidizing gas if two-substance atomizers are used, particular preference being given to nitrogen, argon or carbon dioxide. The liquid to be sprayed can be supplied to such nozzles under pressure. The liquid to be sprayed can be atomized by decompressing it in the die bore on attainment of a particular minimum velocity. In addition, it is also possible to use one-substance nozzles for the inventive purpose, for example slot dies or impingement chambers (full-cone nozzles) (for example from Düsen-Schlick GmbH, Germany, or from Spraying Systems Deutschland GmbH, Germany). Such nozzles are also described in EP 0 534 228 A1 and EP 1 191 051 A2.

The postcrosslinkers are typically used in the form of an aqueous solution. When exclusively water is used as the solvent, a surfactant or deagglomeration assistant is advantageously added to the postcrosslinker solution or actually to the base polymer. This improves the wetting performance and reduces the tendency to form lumps.

All anionic, cationic, nonionic and amphoteric surfactants are suitable as deagglomeration assistants, but preference is given to nonionic and amphoteric surfactants for skin compatible reasons. The surfactant may also comprise nitrogen. For example, sorbitan monoesters, such as sorbitan monococoate and sorbitan monolaurate, or ethoxylated variants thereof, for example Polysorbat 20®, are added. Further suitable deagglomeration assistants are the ethoxylated and alkoxylated derivatives of 2-propylheptanol, which are sold under the Lutensol XL® and Lutensol XP® brands (BASF SE, Carl-Bosch-Strasse 38, 67056 Ludwigshafen, Germany).

The deagglomeration assistant can be metered in separately or added to the postcrosslinker solution. Preference is given to simply adding the deagglomeration assistant to the postcrosslinker solution.

The amount of the deagglomeration assistant used, based on base polymer, is, for example, from 0 to 0.1% by weight, preferably from 0 to 0.01% by weight, more preferably from 0 to 0.002% by weight. The deagglomeration assistant is preferably metered in such that the surface tension of an aqueous extract of the swollen base polymer and/or of the swollen postcrosslinked superabsorbent at 23° C. is at least 0.060 N/m, preferably at least 0.062 N/m, more preferably at least 0.065 N/m, and advantageously at most 0.072 N/m.

The aqueous postcrosslinker solution may, as well as the at least one postcrosslinker, also comprise a cosolvent. The content of nonaqueous solvent or total amount of solvent can be used to adjust the penetration depth of the postcrosslinker into the polymer particles. Industrially readily available cosolvents are $C_1$-$C_6$-alkohols such as methanol, ethanol, n-propanol, isopropanol, n-butanol, sec-butanol, tert-butanol or 2-methyl-1-propanol, C2-C5-diols such as ethylene glycol, 1,2-propylene glycol or 1,4-butanediol, ketones such as acetone, or carboxylic esters such as ethyl acetate. A disadvantage of some of these cosolvents is that they have typical intrinsic odors.

The cosolvent itself is ideally not a postcrosslinker under the reaction conditions. However, it may arise in the boundary case and depending on the residence time and temperature that the cosolvent contributes partly to crosslinking. This is the case especially when the postcrosslinker is relatively sluggish and therefore can also be its own cosolvent, as, for example, in the case of use of cyclic carbonates of the general formula (IV), diols of the general formula (IIIa) or polyols of the general formula (IIIb). Such postcrosslinkers can be used in a mixture with more reactive postcrosslinkers or else in the function as a cosolvent, since the actual postcrosslinking reaction can then be carried out at lower temperatures and/or with shorter residence times than in the absence of the more reactive crosslinker. Since the cosolvent is used in relatively large amounts and also remains partly in the product, it must not be toxic.

Also suitable as cosolvents in the process according to the invention are the diols of the general formula (IIa), the polyols of the general formula (IIb), and the cyclic carbonates of the general formula (III). They fulfill this function in the presence of a reactive postcrosslinker of the general formula (I) and/or (IV) and/or of a di- or triglycidyl compound. Preferred cosolvents in the process according to the invention are, however, especially the diols of the general formula (IIa), especially when a reaction of the hydroxyl groups is hindered sterically by neighboring groups. Although such diols are also suitable in principle as postcrosslinkers, this requires significantly higher reaction temperatures or if appropriate higher use amounts than for sterically unhindered diols.

Particularly preferred combinations of low-reactivity postcrosslinker as a cosolvent and reactive postcrosslinker are combinations of preferred polyhydric alcohols, diols of the general formula (IIa) and polyols of the general formula (IIb), with amide acetals or carbamates of the general formula (I).

Suitable combinations are, for example, 2-oxazolidone/1, 2-propanediol and N-(2-hydroxyethyl)-2-oxazolidone/1,2-propanediol, and also ethylene glycol diglycidyl ether/1,2-propanediol.

Very particularly preferred combinations are 2-oxazolidone/1,3-propanediol and N-(2-hydroxyethyl)-2-oxazolidone/1,3-propanediol.

Further preferred combinations are those with ethylene glycol diglycidyl ether or glyceryl di- or triglycidyl ether with the following solvents, cosolvents or cocrosslinkers: isopropanol, 1,3-propanediol, 1,2-propylene glycol or mixtures thereof.

Further preferred combinations are those with 2-oxazolidone or (2-hydroxyethyl)-2-oxazolidone in the following solvents, cosolvents or cocrosslinkers: isopropanol, 1,3-propanediol, 1,2-propylene glycol, ethylene carbonate, propylene carbonate or mixtures thereof.

Frequently, the concentration of the cosolvent in the aqueous postcrosslinker solution is from 15 to 50% by weight, preferably from 15 to 40% by weight, more preferably from 20 to 35% by weight, based on the postcrosslinker solution. In the case of cosolvents of only limited water miscibility, the aqueous postcrosslinker solution will advantageously be adjusted such that only one phase is present, if appropriate by lowering the concentration of the cosolvent.

In a preferred embodiment, no cosolvent is used. The postcrosslinker is then employed only as a solution in water, if appropriate with addition of a deagglomeration assistant.

The concentration of the at least one postcrosslinker in the aqueous postcrosslinker solution is typically from 1 to 20% by weight, preferably from 1.5 to 10% by weight, more preferably from 2 to 5% by weight, based on the postcrosslinker solution.

The total amount of the postcrosslinker solution based on base polymer is typically from 0.3 to 15% by weight, preferably from 2 to 6% by weight.

The actual surface postcrosslinking by reaction of the surface postcrosslinker with functional groups at the surface of the base polymer particles is usually carried out by heating the base polymer wetted with surface postcrosslinker solution, typically referred to as "drying" (but not to be confused with the above-described drying of the polymer gel from the polymerization, in which typically very much more liquid has to be removed). The drying can be effected in the mixer itself, by heating the jacket, by means of heat exchange surfaces or by blowing in warm gases. Simultaneous admixing of the superabsorbent with surface postcrosslinker and drying can be effected, for example, in a fluidized bed drier. The drying is, however, usually carried out in a downstream drier, for example a tray drier, a rotary tube oven, a paddle or disk drier or a heatable screw. Suitable driers are, for example, obtainable as Solidair® or Torusdisc® driers from Bepex International LLC, 333 N.E. Taft Street, Minneapolis, Minn. 55413, U.S.A., or as paddle driers or else as fluidized bed driers from Nara Machinery Co., Ltd., European Branch, Europaallee 46, 50226 Frechen, Germany.

It is possible to heat the polymer particles by means of contact surfaces in a downstream drier for the purpose of drying and performing the surface postcrosslinking, or by means of warm inert gas supply, or by means of a mixture of one or more inert gases with steam, or only with steam alone. In the case of supply of the heat by means of contact surfaces, it is possible to perform the reaction under inert gas at slightly or completely reduced pressure. In the case of use of steam for direct heating of the polymer particles, it is desirable in accordance with the invention to operate the drier under standard pressure or elevated pressure. In this case, it may be advisable to split up the postcrosslinking step into a heating step with steam and a reaction step under inert gas but without steam. This can be achieved in one or more apparatuses. According to the invention, the polymer particles can be heated with steam as early as in the postcrosslinking mixer. The base polymer used may still have a temperature of from 10 to 120° C. from preceding process steps; the postcrosslinker solution may have a temperature of from 0 to 70° C. In particular, the postcrosslinker solution can be heated to reduce the viscosity.

Preferred drying temperatures are in the range from 100 to 250° C., preferably from 120 to 220° C., more preferably from 130 to 210° C., most preferably from 150 to 200° C. The preferred residence time at this temperature in the reaction mixer or drier is preferably at least 10 minutes, more preferably at least 20 minutes, most preferably at least 30 minutes, and typically at most 60 minutes. Typically, the drying is conducted such that the superabsorbent has a residual moisture content of generally at least 0.1% by weight, preferably at least 0.2% by weight and most preferably at least 0.5% by weight, and generally at most 15% by weight, preferably at most 10% by weight and more preferably at most 8% by weight.

The postcrosslinking may take place under standard atmospheric conditions. "Standard atmospheric conditions" means that no technical precautions are taken in order to reduce the partial pressure of oxidizing gases, such as that of atmospheric oxygen, in the apparatus in which the postcrosslinking reaction predominantly takes place (the "postcrosslinking reactor", typically the drier). However, preference is given to performing the postcrosslinking reaction under reduced partial pressure of oxidizing gases. Oxidizing gases are substances which, at 23° C., have a vapor pressure of at least 1013 mbar and act as oxidizing agents in combustion processes, for example oxygen, nitrogen oxide and nitrogen dioxide, especially oxygen. The partial pressure of oxidizing gases is preferably less than 140 mbar, preferably less than 100 mbar, more preferably less than 50 mbar, most preferably less than 10 mbar. When the thermal postcrosslinking is carried out at ambient pressure, i.e. at a total pressure around 1013 mbar, the total partial pressure of the oxidizing gases is determined by their proportion by volume. The proportion of the oxidizing gases is preferably less than 14% by volume, preferably less than 10% by volume, more preferably less than 5% by volume, most preferably less than 1% by volume.

The postcrosslinking can be carried out under reduced pressure. i.e. at a total pressure of less than 1013 mbar. The total pressure is typically less than 670 mbar, preferably less than 480 mbar, more preferably less than 300 mbar, most preferably less than 200 mbar. When drying and postcrosslinking are carried out under air with an oxygen content of 20.8% by volume, the partial oxygen pressures corresponding to the abovementioned total pressures are 139 mbar (670 mbar), 100 mbar (480 mbar), 62 mbar (300 mbar) and 42 mbar (200 mbar), the particular total pressures being in the brackets. Another means of lowering the partial pressure of oxidizing gases is the introduction of nonoxidizing gases, especially inert gases, into the apparatus used for postcrosslinking. Suitable inert gases are substances which are present in gaseous form in the postcrosslinking drier at the postcrosslinking temperature and the given pressure and do not have an oxidizing action on the constituents of the drying polymer particles under these conditions, for example nitrogen, carbon dioxide, argon, steam, preference being given to nitrogen. The amount of inert gas is generally from 0.0001 to 10 m$^3$, preferably from 0.001 to 5 m$^3$, more preferably from 0.005 to 1 m$^3$ and most preferably from 0.005 to 0.1 m$^3$, based on 1 kg of superabsorbent.

In the process according to the invention, the inert gas, if it does not comprise steam, can be blown into the postcrosslinking drier via nozzles; however, particular preference is given to adding the inert gas to the polymer particle stream via nozzles actually within or just upstream of the mixer, by admixing the superabsorbent with surface postcrosslinker.

It will be appreciated that vapors of cosolvents removed from the drier can be condensed again outside the drier and if appropriate recycled.

In a preferred embodiment of the present invention, polyvalent cations are applied to the particle surface in addition to the postcrosslinkers before, during or after the postcrosslinking. This is in principle a further surface postcrosslinking by means of ionic noncovalent bonds, but is occasionally also referred to as "complexation" with the metal ions in question or simply as "coating" with the substances in question (the "complexing agent").

This application of polyvalent cations is effected by spray application of solutions of di- or polyvalent cations, usually di-, tri- or tetravalent metal cations, but also polyvalent cations such as polymers formed, in a formal sense, entirely or partly from vinylamine monomers, such as partly or fully hydrolyzed polyvinylamide (so-called "polyvinylamine"), whose amine groups are always—even at very high pH values—present partly in protonated form to give ammonium groups. Examples of usable divalent metal cations are especially the divalent cations of metals of groups 2 (especially Mg, Ca, Sr, Ba), 7 (especially Mn), 8 (especially Fe), 9 (especially Co), 10 (especially Ni), 11 (especially Cu) and 12 (especially Zn) of the Periodic Table of the Elements. Examples of usable trivalent metal cations are especially the trivalent cations of metals of groups 3 including the lanthanides (especially Sc, Y, La, Ce). 8 (especially Fe), 11 (especially Au), 13 (especially Al) and 14 (especially Bi) of the Periodic Table of the Elements. Examples of usable tetravalent cations are especially the tetravalent cations of metals from the lanthanides (especially Ce) and group 4 (especially Ti, Zr, Hf) of the Periodic Table of the Elements. The metal cations can be used either alone or in a mixture with one another. Particular preference is given to the use of trivalent metal cations. Very particular preference is given to the use of aluminum cations.

Among the metal cations mentioned, suitable metal salts are all of those which possess sufficient solubility in the solvent to be used. Particularly suitable metal salts are those with weakly complexing anions, for example chloride, nitrate and sulfate, hydrogensulfate, carbonate, hydrogencarbonate, nitrate, phosphate, hydrogenphosphate, or dihydrogenphosphate. Preference is given to salts of mono- and dicarboxylic acids, hydroxy acids, ketoacids and amino acids, or basic salts. Preferred examples include acetates, propionates, tartrates, maleates, citrates, lactates, malates, succinates. Equally preferred is the use of hydroxides. Particular preference is given to the use of 2-hydroxycarbonic salts such as citrates and lactates. Examples of particularly preferred metal salts are alkali metal and alkaline earth metal aluminates and hydrates thereof, for instance sodium aluminate and hydrates thereof, alkali metal and alkaline earth metal lactates and citrates and hydrates thereof, aluminum acetate, aluminum propionate, aluminum citrate and aluminum lactate.

The cations and salts mentioned may be used in pure form or as a mixture of different cations or salts. The salts of the di- and/or trivalent metal cation used may comprise further secondary constituents such as stiu unneutralized carboxylic acid and/or alkali metal salts of the neutralized carboxylic acid. Preferred alkali metal salts are those of sodium and potassium, and those of ammonium. They are typically used in the form of an aqueous solution which is obtained by dissolving the solid salts in water, or is preferably obtained directly as such, which avoids any drying and purification steps. Advantageously, it is also possible to use the hydrates of the salts mentioned, which often dissolve more rapidly in water than the anhydrous salts.

The amount of metal salt used is generally at least 0.001% by weight, preferably at least 0.01% by weight and more preferably at least 0.1% by weight, for example at least 0.4% by weight, and generally at most 5% by weight, preferably at most 2.5% by weight and more preferably at most 1% by weight, for example at most 0.7% by weight, based in each case on the mass of the base polymer.

The salt of the trivalent metal cation can be used in the form of a solution or suspension. The solvents used for the metal salts may be water, alcohols, DMF, DMSO, and mixtures of these components. Particular preference is given to water and water/alcohol mixtures, for example water/methanol, water/1,2-propanediol and water/1,3-propanediol.

The base polymer is treated with a solution of a divalent or polyvalent cation in the same manner as that with surface postcrosslinker, including the drying step. Surface postcrosslinker and polyvalent cation can be sprayed on in a combined solution or as separate solutions. The spray application of the metal salt solution to the superabsorbent particles can be effected either before or after the surface postcrosslinking. In a particularly preferred process, the spray application of the metal salt solution is effected in the same step as the spray application of the crosslinker solution, both solutions being sprayed on separately and successfully or simultaneously through two nozzles, or crosslinker and metal salt solution may be sprayed on together through one nozzle.

Especially when a trivalent or higher-valency metal cation such as aluminum is used for complexation, a basic salt of a divalent metal cation or a mixture of such salts is also optionally added. Basic salts are salts which are suitable for increasing the pH of an aqueous acidic solution, preferably 0.1 N hydrochloric acid. Basic salts are typically salts of a strong base with a weak acid.

The divalent metal cation of the optional basic salt is preferably a metal cation of group 2 of the Periodic Table of the Elements, more preferably calcium or strontium, most preferably calcium.

The basic salts of the divalent metal cations are preferably salts of weak inorganic acids, of weak organic acids and/or salts of amino acids, more preferably hydroxides, hydrogencarbonates, carbonates, acetates, propionates, citrates, gluconates, lactates, tartrates, malates, succinates, maleates and/or fumarates, most preferably hydroxides, hydrogencarbonates, carbonates, propionates and/or lactates. The basic salt is preferably water-soluble. Water-soluble salts are salts which, at 20° C., have a water solubility of at least 0.5 g of salt per liter of water, preferably at least 1 g of salt of l per water, preferentially at least 10 g of salt per l of water, more preferably at least 100 g of salt per l of water, most preferably at least 200 g of salt per l of water. However, it is also possible in accordance with the invention to use those salts which have this minimum solubility at the spray application temperature of the spray solution. It is advantageously also possible to use the hydrates of the salts mentioned, which often dissolve more rapidly in water than the anhydrous salts.

Suitable basic salts of divalent metal cations are, for example, calcium hydroxide, strontium hydroxide, calcium hydrogencarbonate, strontium hydrogencarbonate, calcium acetate, strontium acetate, calcium propionate, calcium lactate, strontium propionate, strontium lactate, zinc lactate, calcium carbonate and strontium carbonate.

When the water solubility is insufficient to prepare a spray solution of the desired concentration, it is also possible to use dispersions of the solid salt in a saturated aqueous solution thereof. For example, it is also possible to use calcium carbonate, strontium carbonate, calcium sulfite, strontium sulfite, calcium phosphate and strontium phosphate as aqueous dispersions.

The amount of basic salt of the divalent metal cation, based on the mass of the base polymer, is typically from 0.001 to 5% by weight, preferably from 0.01 to 2.5% by weight, preferentially from 0.1 to 1.5% by weight, more preferably from 0.1 to 1% by weight, most preferably from 0.4 to 0.7% by weight.

The basic salt of the divalent metal cation can be used in the form of a solution or suspension. Examples thereof are calcium lactate solutions or calcium hydroxide suspensions. Typically, the salts are sprayed on with an amount of water of not more than 15% by weight, preferably of not more than 8% by weight, more preferably of not more than 5% by weight, most preferably of not more than 2% by weight, based on the superabsorbent.

Preference is given to spraying an aqueous solution of the basic salt onto the superabsorbent. Conveniently, the basic salt is added simultaneously with the surface postcrosslinker, the complexing agent or as a further constituent of the solutions of these agents. For these basic salts, preference is given to addition in a mixture with the complexing agent. When the solution of the basic salt is not miscible with the solution of the complexing agent without precipitation, the solutions can be sprayed on separately in succession or simultaneously from two nozzles.

A reducing compound is optionally also added to the superabsorbent. Examples of reducing compounds are hypophosphites, sulfinates or sulfites. Preference is given to the addition of a sulfinic acid derivative, especially of a compound of the formula (V)

in which
M is a hydrogen atom, an ammonium ion, a monovalent metal ion or an equivalent of a divalent metal ion of groups 1, 2, 8, 9, 10, 12 or 14 of the Periodic Table of the Elements;
$R^{27}$ is OH or $NR^{30}R^{31}$ where $R^{30}$ and $R^{31}$ are each independently H or $C_1$-$C_6$-alkyl;
$R^{28}$ is H or an alkyl, alkenyl, cycloalkyl or aryl group, where this group optionally has 1, 2 or 3 substituents which are each independently selected from $C_1$-$C_6$-alkyl. OH, O—$C_1$-$C_8$-alkyl, halogen and $CF_3$; and
$R^{29}$ is COOM, $SO_3M$, $COR^{30}$, $CONR^{30}R^{31}$ or $COOR^{30}$, where M, $R^{30}$ and $R^{31}$ are each as defined above or, when $R^{28}$ is aryl which is optionally substituted as specified above, is also H,
salts thereof or mixtures of such compounds and/or salts thereof.

In the above formula, alkyl represents straight-chain or branched alkyl groups which have preferably 1-6, especially 1-4 carbon atoms. Examples of alkyl groups are methyl, ethyl, n-propyl isopropyl, n-butyl, t-butyl, n-hexyl etc. The same applies to the alkyl groups in O-alkyl. Alkenyl represents straight-chain or branched alkenyl groups which preferably have 3-8 carbon atoms, especially 3-6 carbon atoms. A preferred alkenyl group is the allyl group. Cycloalkyl represents especially $C_1$-$C_8$-cycloalkyl, particular preference being given to cyclopentyl and cyclohexyl. Aryl (including in aralkyl) preferably represents phenyl or naphthyl. When the aryl radical represents a phenyl group and is substituted, it preferably has two substituents. These are especially present in the 2 and/or 4 position.

Halogen represents F, Cl, Br and I, preferably Cl and Br.
M is preferably an ammonium ion, alkali metal ion or one equivalent of an alkaline earth metal ion or zinc ion. Suitable alkali metal ions are especially sodium and potassium ions; suitable alkaline earth metal ions are in particular magnesium, strontium and calcium ions.

$R^{27}$ is preferably a hydroxyl or amino group.
$R^{28}$ is preferably a hydrogen atom or an alkyl or aryl group which may be substituted as above. It preferably has one or two hydroxyl and/or alkoxy substituents.
$R^{29}$ is preferably either COOM or $COOR^{30}$ (M and $R^{30}$ are each as defined above) or, when $R^{27}$ is aryl which may be substituted as specified above, is also a hydrogen atom.

In a preferred embodiment, compounds added to the superabsorbent are of the above formula (V) in which M is an alkali metal ion or one equivalent of an alkaline earth metal or zinc ion; $R^{27}$ is a hydroxyl or amino group; $R^{28}$ is H or alkyl and $R^{29}$ is COOM or $COOR^{30}$, where, when $R^{29}$ is COOM. M in this COOM radical is H, an alkali metal ion or one equivalent of an alkaline earth metal ion and, when $R^{29}$ is $COOR^{30}$, $R^{30}$ is $C_1$-$C_6$-alkyl.

In a further preferred embodiment, the compounds added to the superabsorbent are of the above formula (V) in which M is an alkali metal ion or one equivalent of an alkaline earth metal or zinc ion; $R^{27}$ is a hydroxyl or amino group; $R^{28}$ is aryl which is optionally substituted as specified above, especially hydroxyphenyl or $C_1$-$C_4$-alkoxyphenyl, and $R^{29}$ is a hydrogen atom.

Groups 1 (H, Li, Na, K, Rb, Cs, Fr), 2 (Be, Mg, Ca, Sr, Ba, Ra), 8 (Fe, Ru, Os), 9 (Co, Rh, Ir), 10 (Ni, Pd, Pt), 12 (Zn, Cd, Hg) and 14 (C, Si, Ge, Sn, Pb) of the Periodic Table of the Elements in the current IUPAC numbering (International Union of Pure and Applied Chemistry, 104 T.W. Alexander Drive, Building 19, Research Triangle Park, N.C. 27709, U.S.A., www.iupac.org), the international organization responsible for nomenclature in the field of chemistry, correspond to groups Ia, IIa, IIb, IVa and VIIIb in the numbering used by CAS (Chemical Abstracts Service, 2540 Olentangy River Road, Columbus, Ohio 43202, U.S.A., www.cas.org).

The sulfinic acid derivatives of the above formula (V) can be added in pure form, but optionally also in the mixture with the sulfite of the corresponding metal ion and of the corresponding sulfonic acid which results in a customary manner from the preparation of such compounds. The preparation of such sulfinic acid derivatives of the above formula is known and is described, for example, in WO 99/18 067 A1. They are also conventional commercial products and are available, for example, in the form of mixtures of the sodium salt of 2-hydroxy-2-sulfinatoacetic acid, the disodium salt of 2-hydroxy-2-sulfonatoacetic acid and sodium bisulfite from L. Brüggemann KG (Salzstrasse 131, 74076 Heilbronn, Germany, www.brueggemann.com) under the names BRÜGGOLIT® FF6M or BRÜGGOLIT® FF7, or alternatively BRUGGOLITE® FF6M or BRUGGOLITE® FF7.

The addition of one or more reducing compounds to the superabsorbent is effected in a customary manner by adding the compound in bulk, as a solution or as a suspension in a solvent or suspension medium during or after the preparation of the superabsorbent. Typically, a solution or suspension of the reducing compound in water or an organic solvent is used, for example in an alcohol or polyol or in mixtures thereof. Examples of suitable solvents or suspension media are water, isopropanol/water, 1,3-propanediol/water and propylene glycol/water, where the mixing mass ratio is preferably from 20:80 to 40:60. A surfactant can be added to the solution or suspension. If reducing compounds are added, they are generally added in an amount of at least 0.0001% by weight, preferably at least 0.001% by weight and more preferably at least 0.025% by weight, for example at least 0.1% by weight or at least 0.3% by weight, and generally at most 3% by weight, preferably at most 2.5% by weight and more preferably at most 1.5% by weight, for example at most 1% by weight or 0.7% by weight, based in each case on the total weight of the superabsorbent.

The reducing compound is generally mixed with the superabsorbent known per se in exactly the same manner as the solution or suspension comprising a surface postcrosslinker which is applied to the superabsorbent for surface postcrosslinking. The reducing compound can be applied to a base polymer as a constituent of the solution applied for surface postcrosslinking or of one of the components thereof, i.e. can be added to the solution of the surface postcrosslinker or to one of the components thereof. The superabsorbent coated with surface postcrosslinker and reducing compound then passes through the further process steps required for surface postcrosslinking, for example a thermally induced reaction of the surface postcrosslinker with the superabsorbent. This process is comparatively simple and economically viable.

If very high stability to discoloration in the course of prolonged storage is essential, the reducing compound is preferably applied after the surface postcrosslinking in a dedicated process step. If it is applied in the form of a solution or suspension, the application is effected to the already surface postcrosslinked superabsorbent in the same manner as the application of the surface postcrosslinker to the base polymer. This is usually, but not necessarily, followed by heating, just like in the surface postcrosslinking, in order to dry the superabsorbent again. The temperature established in this drying step is then, however, generally at most 110° C., preferably at most 100° C. and more preferably at most 90° C., in order to prevent undesired reactions of the reducing compound. The temperature is established such that, in view of the residence time in the drying unit, the desired water content of the superabsorbent is achieved. It is also entirely possible and convenient to add the reducing compound individually or together with other customary assistants, for example dust binders, anticaking agents or water for remoistening the superabsorbent, as described below for these assistants, for example in a cooler connected downstream of the surface postcrosslinking. The temperature of the polymer particles in this case is between 0° C. and 190° C., preferably less than 160° C., more preferably less than 130° C., even more preferably less than 100° C., and most preferably less than 70° C. If appropriate, the polymer particles are cooled after coating rapidly to temperatures below the decomposition temperature of the reducing compound.

If, after the surface postcrosslinking and/or treatment with complexing agent, a drying step is carried out, it is advantageous but not absolutely necessary to cool the product after the drying step. The cooling can be effected continuously or batchwise; to this end, the product is conveyed continuously into a cooler connected downstream of the drier. To this end, it is possible to use any apparatus known for removal of heat from pulverulent solids, especially any apparatus mentioned above as a drying apparatus, provided that it is not charged with a heating medium but rather with a cooling medium, for instance with cooling water, such that no heat is introduced into the superabsorbent via the walls and, according to the construction, also via the stirrer units or other heat exchange surfaces, but rather removed therefrom. Preference is given to the use of coolers in which the product is moved, i.e. cooled mixers, for example paddle coolers or disk coolers. The superabsorbent can also be cooled in a fluidized bed by blowing in a cooled gas such as cold air. The cooling conditions are established such that a superabsorbent with the temperature desired for further processing is obtained. Typically, a mean residence time in the cooler of generally at least 1 minute, preferably at least 3 minutes and more preferably at least 5 minutes, and generally at most 6 hours, preferably at most 2 hours and more preferably at most 1 hour, is established, and the cooling performance is such that the resulting product has a temperature of generally at least 0° C., preferably at least 10° C. and more preferably at least 20° C., and generally at most 100° C., preferably at most 80° C. and more preferably at most 60° C.

The surface postcrosslinked superabsorbent is optionally ground and/or screened in a customary manner. Grinding is typically not required here, but screening-off of agglomerates or fines formed is usually appropriate to establish the desired particle size distribution of the product. Agglomerates and fines are either discarded or preferably recycled into the process in a known manner at a suitable point; agglomerates after comminution. The particle sizes desired for surface postcrosslinked superabsorbents are the same as for base polymers.

It is optionally possible to additionally apply to the surface of the superabsorbent particles, whether unpostcrosslinked or postcrosslinked, in any process step of the preparation process, if required, all known coatings, such as film-forming polymers, thermoplastic polymers, dendrimers, polycationic polymers (for example polyvinylamine, polyethyleneimine or polyallylamine), water-insoluble polyvalent metal salts, for example magnesium carbonate, magnesium oxide, magnesium hydroxide, calcium carbonate, calcium sulfate or calcium phosphate, all water-soluble mono- or polyvalent metal salts known to those skilled in the art, for example aluminum sulfate, sodium salts, potassium salts, zirconium salts or iron salts, or hydrophilic inorganic particles such as clay minerals, fumed silica, colloidal silica sols, for example Levasil®, titanium dioxide, aluminum oxide and magnesium oxide. Examples of useful alkali metal salts are sodium and potassium sulfate, and sodium and potassium lactates, citrates and sorbates. This allows additional effects, for example a reduced caking tendency of the end product or of the intermediate in the particular process step of the production process, improved processing properties or a further enhanced saline flow conductivity (SFC), to be achieved. When the additives are used and sprayed on in the form of dispersions, they are preferably used as aqueous dispersions, and preference is given to additionally applying an antidusting agent to fix the additive on the surface of the superabsorbent. The antidusting agent is then either added directly to the dispersion of the inorganic pulverulent additive; optionally, it can also be added as a separate solution before, during or after the application of the inorganic pulverulent additive by spray application. Most preferred is the simultaneous spray application of postcrosslinker, antidusting agent and pulverulent inorganic additive in the postcrosslinking step. In a further preferred process variant, the antidusting agent is, however, added separately in the cooler, for example by spray application from above, below or from the side. Particularly suitable antidusting agents which can also serve to fix pulverulent inorganic additives on the surface of the superabsorbent particles are polyethylene glycols with a molecular weight of from 400 to 20 000 g/mol, polyglycerol, 3- to 100-tuply ethoxylated polyols such as trimethylolpropane, glycerol, sorbitol and neopentyl glycol. Particularly suitable are 7- to 20-tuply ethoxylated glycerol or trimethylolpropane, for example Polyol TP 70® (Perstorp, Sweden). The latter have, more particularly, the advantage that they lower the surface tension of an aqueous extract of the superabsorbent particles only insignificantly.

It is equally possible to adjust the inventive superabsorbent to a desired water content by adding water.

Optionally, the inventive superabsorbents are provided with further additives which stabilize against discoloration. Examples are especially known stabilizers against discoloration, especially reducing substances. Among these, preference is given to solid or dissolved salts of phosphinic acid ($H_3PO_2$) and to this acid itself. For example, all phosphinates of the alkali metals are suitable, including those of ammonium, and of the alkaline earth metals. Particular preference is given to aqueous solutions of phosphinic acid which comprise phosphinate ions and at least one cation selected from sodium, potassium, ammonium, calcium, strontium, aluminum, magnesium. Equally preferred are salts of phosphinic acid ($H_3PO_3$) and this acid itself. For example, all primary and secondary phosphonates of the alkali metals, including of ammonium, and of the alkaline earth metals are suitable. Particular preference is given to aqueous solutions of phosphinic acid which comprise primary and/or secondary phosphonate ions and at least one cation selected from sodium, potassium, calcium, strontium.

All coatings, solids, additives and assistants can each be added in separate process steps, but the most convenient method is usually to add them—if they are not added during the admixing of the base polymer with surface postcrosslinkers—to the superabsorbent in the cooler, for instance by spray application of a solution or addition in finely divided solid form or in liquid form.

The L value of the superabsorbent (CIE color number) is, in the unstored state) typically at least 75, preferably at least 80, more preferably at least 85 and at most 100.

The a value of the superabsorbent (CIE color number) is, in the unstored state, typically from −2.5 to +2.5, preferably from −2.0 to +2.0, more preferably from −1.5 to +1.5.

The b value of the superabsorbent (CIE color number) in the unstored state is typically from 0 to 10.

The present invention further provides the superabsorbent which is obtainable by the process according to the invention and which, even and specifically in the case of a relatively high content of iron ions in the monomer mixture, has a low residual monomer content compared to other superabsorbents while also being comparatively colorless.

The inventive superabsorbent generally has a centrifuge retention capacity (CRC) of at least 5 µg, preferably of at least 10 g/g and more preferably of at least 20 g/g. Further suitable minimum values of the CRC are, for example, 25 g/g, 30 g/g or 35 µg. It is typically not more than 40 g/g. A typical CRC range for surface postcrosslinked superabsorbents is from 28 to 33 g/g.

When it is surface postcrosslinked, the inventive superabsorbent typically has an absorbency under load (AUL0.7 psi, see below for test method) of at least 18 g/g, preferably at least 20 g/g, preferentially at least 22 g/g, more preferably at least 23 g/g, most preferably at least 24 g/g, and typically not more than 30 g/g.

The inventive superabsorbent additionally has a saline flow conductivity (SFC, see below for test method) of at least $10 \times 10^{-7}$ cm$^3$ s/g, preferably at least $30 \times 10^{-7}$ cm$^3$ s/g, preferentially at least $50 \times 10^{-7}$ cm$^3$ s/g, more preferably at least $80 \times 10^{-7}$ cm$^3$ s/g, most preferably at least $100 \times 10^{-7}$ cm$^3$ s/g, and typically not more than $1000 \times 10^{-7}$ cm$^3$ s/g.

The present invention further provides hygiene articles comprising inventive superabsorbents, preferably ultrathin diapers, comprising an absorbent layer consisting of from 50 to 100% by weight, preferably from 60 to 100% by weight, preferentially from 70 to 100% by weight, more preferably from 80 to 100% by weight, most preferably from 90 to 100% by weight, of inventive superabsorbents, excluding, of course, the shell of the absorbent layer.

The inventive superabsorbents are also very particularly advantageous for production of laminates and composite structures, as described, for example, in US 2003/0181115 and US 2004/0019342. In addition to the hotmelt adhesives described in both documents for production of such novel absorbent structures and especially to the fibers composed of hotmelt adhesives which are described in US 2003/0181115 and to which the superabsorbent particles are bonded, the inventive superabsorbents are also suitable for producing entirely analogous structures using UV-crosslinkable hotmelt adhesives, which are sold, for example, as AC Resin® (BASF SE, Carl-Bosch-Strasse 38, 67056 Ludwigshafen, Germany). These UV-crosslinkable hotmelt adhesives have the advantage of being processable even at from 120 to 140° C.; they are therefore better compatible with many thermoplastic substrates. A further significant advantage is that UV-crosslinkable hotmelt adhesives are toxicologically entirely safe and also do not cause any vaporization in the hygiene articles. A very significant advantage in connection with the inventive superabsorbents is the property of the UV-crosslinkable hotmelt adhesives of not tending to yellow during processing and crosslinking. This is especially advantageous when ultrathin or partly transparent hygiene articles are to be produced. The combination of the inventive superabsorbents with UV-crosslinkable hotmelt adhesives is therefore particularly advantageous. Suitable UV-crosslinkable hotmelt adhesives are, for example, described in EP 0 377 199 A2, EP 0 445 641 A1, U.S. Pat. No. 5,026,806, EP 0 655 465 A1 and EP 0 377 191 A2.

The inventive superabsorbent can also be used in other fields of industry in which liquids, especially water or aqueous solutions, are absorbed. These fields are, for example, storage, packaging, transport (as constituents of packaging material for water- or moisture-sensitive articles, for instance for flower transport, and also as protection against mechanical effects); animal hygiene (in cat litter); food packaging (transport of fish, fresh meat; absorption of water, blood in fresh fish or meat packaging); medicine (wound plasters, water-absorbing material for burn dressings or for other weeping wounds), cosmetics (carrier material for pharmaceutical chemicals and medicaments, rheumatic plasters, ultrasonic gel, cooling gel, cosmetic thickeners, sunscreen); thickeners for oil/water or water/oil emulsions; textiles (moisture regulation in textiles, shoe insoles, for evaporative cooling, for instance in protective clothing, gloves, headbands); chemical engineering applications (as a catalyst for organic reactions, for immobilization of large functional molecules such as enzymes, as an adhesive in agglomerations, heat stores, filtration aids, hydrophilic components in polymer laminates, dispersants, liquefiers); as assistants in powder injection molding, in the building and construction industry (installation, in loam-based renders, as a vibration-inhibiting medium, assistants in tunnel excavations in water-rich ground, cable sheathing); water treatment, waste removal, water removal (deicers, reusable sand bags); cleaning; agrochemical industry (irrigation, retention of melt water and dew deposits, composting additive, protection of forests from fungal/insect infestation, retarded release of active ingredients to plants); for firefighting or for fire protection; coextrusion agents in thermoplastic polymers (for example for hydrophilization of multilayer films); production of films and thermoplastic moldings which can absorb water (e.g. films which store rain and dew for agriculture; films comprising superabsorbents for maintaining freshness of fruit and vegetables which are packaged in moist films; superabsorbent-polystyrene coextrudants, for example for packaging foods such as meat, fish, poultry, fruit and vegetables); or as a carrier substance in active ingredient formulations (pharmaceuticals, crop protection).

The inventive articles for absorption of fluid differ from known examples in that they comprise the inventive superabsorbent.

Also found has been a process for producing articles for absorption of fluid, especially hygiene articles, which comprises using at least one inventive superabsorbent in the production of the article in question. In addition, processes for producing such articles using superabsorbents are known.

Test Methods

The superabsorbent is tested by the test methods described below.

The standard test methods referred to as "VVSP" described below are described in: "Standard Test Methods for the Nonwovens Industry". 2005 edition, published jointly by the Worldwide Strategic Partners EDANA (European Disposables and Nonwovens Association, Avenue Eugene Plasky, 157, 1030 Brussels, Belgium, www.edana.org) and INDA (Association of the Nonwoven Fabrics Industry, 1100 Crescent Green, Suite 115, Cary, N.C. 27518, U.S.A., www.inda.org). This publication is obtainable both from EDANA and from INDA.

All methods described below should, unless stated otherwise, be carried out at an ambient temperature of 23±2° C. and a relative air humidity of 50±10%. The superabsorbent particles are mixed thoroughly before the measurement unless stated otherwise.

Centrifuge Retention Capacity (CRC)

The centrifuge retention capacity of the superabsorbent is determined by the standard test method No. VVSP 241.5-02 "Centrifuge retention capacity".

Absorbency Under a Load of 0.3 psi (AUL0.3 psi)

The absorbency under a load of 2068 Pa (0.3 psi) of the superabsorbent is determined by the standard test method No. WSP 242.2-05 "Absorption under pressure".

Absorbency Under a Load of 0.7 psi (AUL0.7 psi)

The absorbency under a load of 4826 Pa (0.7 psi) of the superabsorbent is determined analogously to the standard test method No. WSP 242.2-05 "Absorption under pressure", except using a weight of 49 g/cm² (leads to a load of 0.7 psi) instead of a weight of 21 g/cm² (leads to a load of 0.3 psi).

Moisture Content of the Superabsorbent (Residual Moisture, Water Content)

The water content of the superabsorbent particles is determined by the standard test method No. WSP 230.2-05 "Moisture content".

Mean Particle Size

The mean particle size of the product fraction is determined by the standard test method No. VVSP 220.2-05 "Particle size distribution".

Residua Monomer Content

The content in the superabsorbent particles of residual monomers is determined by standard test method No. VVSP 210.2-05 "Residual Monomers".

CIE Color Number (L a b)

The color measurement is carried out according to CIELAB method (Hunterlab, volume 8, 1996, book 7, pages 1 to 4) with a "LabScan XE S/N LX17309" colorimeter (HunterLab, Reston, U.S.A.). This method describes the colors via the coordinates L, a and b of a three-dimensional system. L indicates the brightness, where L=0 means black and L=100 white. The values of a and b indicate the position of the color on the red/green and yellow/blue color axes, where +a represents red, −a represents green, +b represents yellow and −b represents blue.

The color measurement corresponds to the three-area method according to DIN 5033-6.

EXAMPLES

Example 1

Preparation of a Base Polymer (Comparative)

A kneader with two Sigma shafts (model LUK 8.0 K2, manufactured by Coperion Werner & Pfleiderer GmbH & Co. KG, Stuttgart, Germany) was purged with nitrogen for inertization and then charged with a mixture, freed of oxygen by sparging with nitrogen, of 5166 g of a 37.7% by weight aqueous sodium acrylate solution, 574 g of acrylic acid and 720 g of demineralized water. Subsequently, 6.2 g of 3-tuply ethoxylated glyceryl triacrylate were added as an internal crosslinker, as were, thereafter, as an initiator, 16.5 g of a 0.75% by weight aqueous ascorbic acid solution, 38.6 g of a 15% by weight aqueous sodium persulfate solution and 3.4 g of a 3% by weight aqueous hydrogen peroxide solution. The kneader was operated at speeds of 98 revolutions per minute on one shaft and at 49 revolutions per minute on the other shaft. Immediately after the addition of the hydrogen peroxide solution, the solution was heated through the heating jacket of the kneader by means of passage of heating fluid (80° C.). As soon as the temperature in the kneader ceased to rise any further, the heating was ended and the polymer gel was allowed to react for a further 14 minutes. Subsequently, the gel was allowed to cool to about 65° C. and removed from the kneader. The gel was dried in portions of 400 g each with a forced-air drier at 160'C for 22 minutes, in the course of which the gel dried in a screen insert through which air at this temperature flowed from below, having been heated by a hot-air blower. The hot air flows through the gel from the bottom upward during this drying. Finally, the dried gel was ground three times on a roll mill (LRC 125/70 model, manufactured by Bauermeister Zerkleinerungstechnik GmbH, Norderstedt, Germany), by successively setting gap widths of 1000 μm, 600 μm and 400 μm. The superabsorbent was screened off, and the screened fraction from 300 to 600 μm was obtained as the base polymer.

Example 2

Comparative

Example 1 was repeated, except that 10.3 g of urea (=0.5% by weight based on acrylic monomer: the sodium acrylate is converted to acrylic acid for the calculation and added to the free acrylic acid. All further statements of amount below were calculated in the same way.) were added to the monomer mixture.

Example 3

Comparative

Example 1 was repeated, except that 20.7 g of urea were added to the monomer mixture (=1.0% by weight based on acrylic monomer).

Example 4

Example 1 was repeated, except that 10.3 g of urea phosphate were added to the monomer mixture (=0.5% by weight based on acrylic monomer).

Example 5

Example 1 was repeated, except that 20.7 g of urea phosphate were added to the monomer mixture (=1.0% by weight based on acrylic monomer).

Example 6

Example 5 was repeated, except that 15 ppm by weight of iron(II) sulfate ($FeSO_4 \cdot 7\ H_2O$) based on acrylic monomer were additionally added to the monomer mixture (=3 ppm by weight of iron ions based on acrylic monomer).

Example 7

Example 5 was repeated, except that 50 ppm by weight of iron(II) sulfate ($FeSO_4 \cdot 7\ H_2O$) based on acrylic monomer were additionally added to the monomer mixture (=10 ppm by weight of iron ions based on acrylic monomer).

Example 8

Preparation of a Base Polymer (Comparative)

A kneader with two Sigma shafts (model LUK 8.0 K2, manufactured by Coperion Werner & Pfleiderer GmbH & Co. KG, Stuttgart, Germany) was purged with nitrogen for inertization and then charged with a mixture, freed of oxygen by sparging with nitrogen, of 4701 g of a 37.7% by weight aqueous sodium acrylate solution, 522 g of acrylic acid and 1237 g of demineralized water. Subsequently, 4.7 g of 3-tuply ethoxylated glyceryl triacrylate were added as an internal crosslinker, as were, thereafter, as an initiator, 15.0 g of a 0.75% by weight aqueous ascorbic acid solution, 35.1 g of a 15% by weight aqueous sodium persulfate solution and 3.1 g of a 3% by weight aqueous hydrogen peroxide solution. The kneader was operated at speeds of 98 revolutions per minute on one shaft and at 49 revolutions per minute on the other shaft. Immediately after the addition of the hydrogen peroxide solution, the solution was heated through the heating jacket of the kneader by means of passage of heating fluid (80° C.). As soon as the temperature in the kneader ceased to rise any further, the heating was ended and the polymer gel was allowed to react for a further 14 minutes. Subsequently, the gel was allowed to cool to about 65° C. and removed from the kneader. The gel was dried in portions of 400 g each with a forced-air drier at 160° C. for 22 minutes, in the course of which the gel dried in a screen insert through which air at this temperature flowed from below, having been heated by a hot-air blower. The hot air flows through the gel from the bottom upward during this drying. Finally, the dried gel was ground three times on a roll mill (LRC 125/70 model, manufactured by Bauermeister Zerkleinerungstechnik GmbH, Norderstedt, Germany), by successively setting gap widths of 1000 μm, 600 μm and 400 μm. The superabsorbent was screened off, and the screened fraction from 300 to 600 μm was obtained as the base polymer.

Example 9

Comparative

Example 8 was repeated, except that 15 ppm by weight of iron(II) sulfate ($FeSO_4 \cdot 7\ H_2O$) based on acrylic monomer were additionally added to the monomer mixture (=3 ppm by weight of iron ions based on acrylic monomer).

Example 10

Comparative

Example 8 was repeated, except that 15 ppm by weight of iron(II) sulfate ($FeSO_4 \cdot 7\ H_2O$) based on acrylic monomer were additionally added to the monomer mixture (=3 ppm by weight of iron ions based on acrylic monomer), and 29 ppm by weight of $KH_2PO_4$ based on acrylic monomer were additionally added.

The properties of the superabsorbent from examples 1 to 10 are compiled in table 1.

The comparison of the examples in table 1 shows that the addition of urea lowers the residual monomer content to a desired level (examples 1, 2 and 3) only from an amount of 1% by weight based on acrylic monomer (=bam, see explanation for table), whereas urea phosphate achieves this already from an amount of 0.5% by weight bam (examples 1, 4 and 5). However, the superabsorbent with 1.0% by weight bam of urea addition shows a tendency toward greater undesired yellowing (increased b color number). In addition, it becomes clear that iron impurities increase the residual monomer content (examples 8 and 9) and lead to a tendency toward greater yellowing (examples 8 and 9, and 1, 6 and 7). The addition of phosphate influences neither the residual monomer content nor the yellowing (examples 9 and 10). The inventive examples show that urea phosphate, in contrast to the urea and phosphate components, even in comparatively small amounts and even in the presence of iron impurities, lowers the residual monomer content very significantly, although there is also a tendency to greater yellowing in the presence of iron.

Example 11

Comparative: Production of a Surface Postcrosslinked Superabsorbent

A food processor (manufacturer: Robert Bosch GmbH, Robert-Bosch-Platz 1; 70839 Gerlingen-Schillerhöhe, Germany, "Profimixx 47/MUM4700" model) with egg beaters was charged with 250 g of the polymer of example 1 and mixed at level 4.10 g of a solution composed of 6.82 g of demineralized water, 2.92 g of isopropanol, 0.25 g of a mixture of equal parts by weight of 1,3-propanediol and N-(2-hydroxyethyl)-2-oxazolidinone and 0.010 g of sorbitan monococoate ("Span® 20") were sprayed by means of a two-substance nozzle (Büchi Labortechnik GmbH, Am Porscheplatz 5, 45127 Essen, Germany, www.buechigmbh.de; item No. 004364, 0.7 mm) operated with nitrogen (pressure 0.25 bar gauge) as carrier gas onto the mixed base polymer within 20 seconds, which was then mixed for a further 2 minutes. The motor was stopped and polymer adhering on the stirring bowl wall and the tool was removed again. Subsequently, the stirring bowl contents were mixed for another 100 seconds.

The polymer was placed onto a metal sheet, spread very homogeneously and dried in a forced-air drying cabinet preheated to 200° C. for 45 minutes. After cooling to room temperature, agglomerates and coarse particles were removed from the surface postcrosslinked superabsorbent by means of a screen of mesh size 850 μm.

Example 12

Example 11 was repeated with the polymer of example 2.

Example 13

Example 11 was repeated with the polymer of example 3.

Example 14

Example 11 was repeated with the polymer of example 4.

Example 15

Example 11 was repeated with the polymer of example 5.

Example 16

Example 11 was repeated with the polymer of example 6.

Example 17

Example 11 was repeated with the polymer of example 7.

Example 18

A laboratory mixer (manufacturer: Waring Products, Inc., Torrington, Conn., U.S.A., model 34 BL 99 (8012)) with two opposite rounded mixing blades and baffles on the lid (comparable results are also achieved in many other mixers with good mixing during the application of the postcrosslinking solution, though it should be ensured that the stirrer units do not comminute the superabsorbent—the stirrer speed should be set correspondingly) was initially charged with 20 g of the polymer of example 8. A disposal syringe was used to add a mixture composed of 0.3 g of isopropanol, 0.7 g of water and 20 mg of ethylene glycol diglycidyl ether (Denacol® EX-810 from Nagase ChemteX Corporation, Osaka, Japan) dropwise to the mixed polymer at a moderate stirrer level of the mixer.

The polymer was subsequently dried on a watchglass in a forced-air drying cabinet at 150° C. for one hour and finally, to remove lumps, screened through a 850 μm screen.

Example 19

Example 18 was repeated with the polymer of example 9.

Example 20

Example 18 was repeated with the polymer of example 10.

The properties of the superabsorbent from examples 11 to 20 are compiled in table 2.

The comparison of the examples in table 2 shows that neither addition of urea, of phosphate or of urea phosphate shows a significant influence on the surface postcrosslinking. The superabsorbents of examples 1 to 10 are merely altered by the surface postcrosslinking as expected for the surface postcrosslinking carried out in each case.

TABLE 1

Surface nonpostcrosslinked superabsorbents

| Example | Urea phosphate [% by wt. bam] | Fe* [% by wt. bam] | Other components [% by wt. bam] | CRC [g/g] | AUL 0.3 psi [g/g] | Residual monomers [ppm by wt.] | Color numbers L | a | b |
|---|---|---|---|---|---|---|---|---|---|
| 1 (Comparative) | — | — | — | 35.7 | 13.1 | 1040 | 92.6 | −0.5 | 4.8 |
| 2 (Comparative) | — | — | urea, 0.5 | 36.0 | 14.5 | 1120 | 92.3 | −0.8 | 6.7 |
| 3 (Comparative) | — | — | urea, 1.0 | 35.5 | 19.4 | 380 | 91.9 | −0.7 | 7.4 |
| 4 | 0.5 | — | — | 33.6 | 15.9 | 390 | 93.0 | −0.8 | 6.1 |
| 5 | 1.0 | — | — | 34.2 | 13.7 | 370 | 92.4 | −0.8 | 6.6 |
| 6 | 1.0 | 0.0003 | — | 35.4 | 12.0 | 220 | 91.0 | −0.3 | 8.5 |
| 7 | 1.0 | 0.0010 | — | 36.0 | 9.7 | 370 | 89.9 | 0.3 | 8.2 |
| 8 (Comparative) | — | — | — | 39.1 | 8.4 | 1660 | 92.7 | −0.5 | 4.9 |
| 9 (Comparative) | — | 0.0003 | — | 40.5 | 7.6 | 2860 | 90.8 | −0.2 | 5.6 |
| 10 (Comparative) | — | 0.0003 | KH$_2$PO$_4$, 0.0029 | | | 2840 | 90.2 | −0.1 | 5.9 |

"bam" ("based on acrylic monomers"): calculated based on the mass of the acrylic acid used, the sodium acrylate used being counted as acrylic acid, i.e. the mass of 1 mol of acrylic acid is counted for the mass of each mole of sodium acrylate.
"n.d.": not determined
*the iron is used in the form of iron(II) sulfate heptahydrate; the table indicates the resulting amount of iron used based on acrylic monomer calculated.

TABLE 2

Surface postcrosslinked superabsorbents

| Example | Urea phosphate [% by wt. bam] | Fe* [% by wt. bam] | Other components [% by wt. bam] | CRC [g/g] | AUL 0.7 psi [g/g] | Color numbers L | a | b |
|---|---|---|---|---|---|---|---|---|
| 11 (Comparative) | — | — | — | 34 | 25 | 93.1 | −1.0 | 5.8 |
| 12 (Comparative) | — | — | urea, 0.5 | 32 | 25 | 92.3 | −1.1 | 7.2 |
| 13 (Comparative) | — | — | urea, 1.0 | 30 | 25 | 91.4 | −0.6 | 8.2 |
| 14 | 0.5 | — | — | 31 | 25 | 92.4 | −1.0 | 6.6 |
| 15 | 1.0 | — | — | 31 | 25 | 92.5 | −0.9 | 7.2 |
| 16 | 1.0 | 0.0003 | — | 30 | 23 | 90.8 | −0.4 | 9.2 |
| 17 | 1.0 | 0.0010 | — | 30 | 24 | 90.0 | 0.2 | 9.0 |
| 18 (Comparative) | — | — | — | 35.3 | 26.5 | n.d. | n.d. | n.d. |

TABLE 2-continued

| | Surface postcrosslinked superabsorbents | | | | | | | |
|---|---|---|---|---|---|---|---|---|
| | Urea phosphate | Fe* | Other components | CRC | AUL 0.7 psi | Color numbers | | |
| Example | [% by wt. bam] | [% by wt. bam] | [% by wt. bam] | [g/g] | [g/g] | L | a | b |
| 19 (Comparative) | — | 0.0003 | — | 36.4 | 23.6 | n.d. | n.d. | n.d. |
| 20 (Comparative) | — | 0.0003 | $KH_2PO_4$, 0.0029 | 36.2 | 24.1 | n.d. | n.d. | n.d. |

"bam": see comment for table 1,
"n.d.": not determined
*the iron is used in the form of iron(II) sulfate heptahydrate; the table indicates the resulting amount of iron used based on acrylic monomer calculated.

The invention claimed is:

1. A polymerization process for preparing superabsorbent particles comprising adding a salt of urea with an inorganic acid to a monomer mixture before or during the polymerization, or to a polymer after the polymerization, but before a heat treatment which follows the polymerization,
   wherein the superabsorbent particles have a L value (CIE color number) of at least 75.

2. The process according to claim 1, wherein the inorganic acid is sulfuric acid, phosphoric acid, or a hydrohalic acid.

3. The process according to claim 2, wherein the salt of urea with an inorganic acid is urea phosphate.

4. The process according to claim 1, wherein an aqueous solution of the monomer mixture is polymerized, the monomer mixture comprising:
   at least one ethylenically unsaturated monomer which bears an acid group and is optionally present at least partly in salt form,
   at least one crosslinker,
   at least one initiator,
   optionally one or more ethylenically unsaturated monomer copolymerizable with the monomer specified under a),
   optionally one or more water-soluble polymer, and
   a salt of urea with an inorganic acid.

5. The process according to claim 4, wherein the inorganic acid is sulfuric acid, phosphoric acid, or a hydrohalic acid.

6. The process according to claim 5, wherein the inorganic acid is phosphoric acid.

7. Superabsorbent particles prepared by the process defined in claim 1.

8. The superabsorbent particles according to claim 7, which is surface postcrosslinked.

9. An article for absorbing fluids, comprising the superabsorbent particles defined in claim 7.

10. The process of claim 1 wherein the superabsorbent particles have an L value (CIE color number) of at least 85 and at most 100.

11. The process of claim 1 wherein the heat treatment is a drying step following the polymerization.

* * * * *